United States Patent
Schmidt et al.

(10) Patent No.: US 8,160,715 B2
(45) Date of Patent: Apr. 17, 2012

(54) MIDDLE EAR FIXATION STRUCTURE

(75) Inventors: Marcus Schmidt, Innsbruck (AT); Claude Jolly, Innsbruck (AT); Stefan B. Nielsen, Innsbruck (AT); Joachim Muller, Estenfeld (DE); Daniel Schaudel, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 79 days.

(21) Appl. No.: 12/849,123

(22) Filed: Aug. 3, 2010

(65) Prior Publication Data

US 2010/0305677 A1 Dec. 2, 2010

Related U.S. Application Data

(62) Division of application No. 11/853,128, filed on Sep. 11, 2007, now Pat. No. 7,792,587.

(60) Provisional application No. 60/825,297, filed on Sep. 12, 2006.

(51) Int. Cl.
*A61N 1/375* (2006.01)

(52) U.S. Cl. .......................................... 607/57; 607/136

(58) Field of Classification Search ................... 607/57, 607/136

See application file for complete search history.

(56) References Cited

U.S. PATENT DOCUMENTS

| | | | |
|---|---|---|---|
| 4,462,402 A * | 7/1984 | Burgio et al. ............. 606/129 |
| 6,205,360 B1 | 3/2001 | Carter et al. ............... 607/57 |
| 6,208,882 B1 | 3/2001 | Lenarz et al. ............. 600/379 |
| 6,285,467 B1 | 9/2001 | Ezumi et al. .............. 358/437 |
| 6,473,651 B1 | 10/2002 | Kuzma et al. .............. 607/57 |
| 6,636,768 B1 | 10/2003 | Harrison ................... 607/57 |
| 7,792,587 B2 * | 9/2010 | Schmidt et al. ............. 607/57 |
| 2001/0056291 A1 | 12/2001 | Zilberman et al. .......... 607/57 |
| 2002/0095063 A1 * | 7/2002 | Kroll et al. ................ 600/25 |
| 2004/0078057 A1 | 4/2004 | Gibson ..................... 607/3 |
| 2005/0216073 A1 | 9/2005 | Jolly et al. |

FOREIGN PATENT DOCUMENTS

| | | |
|---|---|---|
| EP | 0109304 | 5/1984 |
| EP | 1470835 | 10/2004 |
| WO | WO 96/17563 | 6/1996 |
| WO | WO2004/014270 | 2/2004 |

OTHER PUBLICATIONS

International Searching Authority, International Search Report, PCT/US2007/078092, dated Jan. 23, 2008.

* cited by examiner

*Primary Examiner* — Carl H Layno
*Assistant Examiner* — Jessica Sarcione
(74) *Attorney, Agent, or Firm* — Sunstein Kann Murphy & Timbers LLP

(57) ABSTRACT

An implantable fixation structure includes a c-shape bone fixation clip adapted to fit over and attach to a bony bridge element in the middle ear of a patient. A c-shape electrode fixation clip is adapted to fit over and attach to an electrode array element in the middle ear of the patient. A connecting bar has a first end connected to the bone fixation clip and a second end connected to the electrode fixation clip. A coupling clip is connected to the connecting bar between the first end and the second end and adapted to fit over and attach to a cochlear implant element and hold the cochlear implant element in a desired position relative to the middle ear of the patient.

6 Claims, 7 Drawing Sheets

MIDDLE EAR FIXATION STRUCTURE

This application is a divisional of U.S. patent application Ser. No. 11/853,128, now U.S. Pat. No. 7,792,587, filed Sep. 11, 2007, which in turn claims priority to U.S. Provisional Patent Application 60/825,297, filed Sep. 12, 2006, the contents of which are hereby incorporated by reference.

FIELD OF THE INVENTION

The present invention relates to cochlear implants and, more particularly, to implantable fixation structures which enable the fixation of one or more cochlear implant elements in a desired position in the middle ear of a patient user.

BACKGROUND ART

Cochlear implants are electronic systems designed to provide useful hearing and improved communication ability to individuals who are profoundly hearing impaired and unable to achieve speech understanding with conventional hearing aids. A typical system includes an implantable stimulator containing electronic circuitry, a coil for power and information transfer, and a stimulation electrode array which is inserted into the inner ear (and perhaps a counter electrode).

In addition to such inner ear applications, there are also concomitant applications to detect and/or measure signals from the stapedius muscle/tendon or other middle ear functions that would be beneficial to the patient and improve the adaptation of cochlear implants. U.S. Pat. No. 6,205,360 (hereby incorporated by reference) describes a middle ear electrode for determining stimulation parameters by detecting the activity of the stapedius muscle. No specific fixation structure is described or suggested for attaching the stapedius monitoring electrode to the stapedius muscle. U.S. Pat. No. 6,636,768 (hereby incorporated by reference) describes another application of an implantable middle ear device including a microphone system which is used together with cochlear implant devices, and where the implantable sensor (i.e. implantable microphone) includes a stationary component and a movable component. The stationary component is implanted so that at least a portion resides within the middle ear and does not come in contact with the movable component. In contrast, the movable component is implanted within the middle ear and is attached to one of the moving elements such as malleus, incus, stapes, oval window or tympanic membrane. But again, no detailed description is provided for the fixation and/or mounting of such implantable devices in the middle ear.

SUMMARY OF THE INVENTION

Many cochlear implant systems need a fixation structure adapted for placement in the middle ear cavity to stably fix of one or more cochlear implant elements such as electronic sensors such as for measuring an electrically evoked stapedius reflex threshold (ESRT), additional implantable electrodes, electro-mechanical actuators (e.g. Floating Mass Transducer), implantable microphone or other arbitrary devices without disrupting the cochlear implant electrodes, effecting injuries in the middle ear, or interfering with the middle ear functions.

Embodiments of the present invention include an implantable fixation structure having a c-shape bone fixation clip adapted to fit over and attach to a bony bridge element in the middle ear of a patient. A c-shape electrode fixation clip is adapted to fit over and attach to an electrode array element in the middle ear of the patient. A connecting bar has a first end connected to the bone fixation clip and a second end connected to the electrode fixation clip. A coupling clip is connected to the connecting bar between the first end and the second end and adapted to fit over and attach to a cochlear implant element and hold the cochlear implant element in a desired position relative to the middle ear of the patient.

The cochlear implant element may include at least one of an electronic sensor, an electro-mechanical actuator, an implantable electrode, an implantable microphone, and/or a stapedius reflex sensor. The coupling clip may be connected perpendicular to the connecting bar.

Embodiments of the present invention also include a cochlear implant system having an implantable fixation structure according to any of the above.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

One problem with fitting young children (as well as some adults) with cochlear implants is the difficulty measuring a comfortable level of response to the electric stimulation. Such persons may not be able to verbally or otherwise express what is a tolerable level of electric stimulation. With respect to such electrical stimulation, electrical potentials may be developed by a sensor which measures contractions and other movements of the stapedius muscle or tendon in the middle ear, and such signals are related to the comfort level of electric stimulation for that person.

Recording an electrically evoked stapedius reflex threshold (ESRT) may allow the objective fitting of the cochlear implant. Recording the ESRT begins by placing a sensing electrode or other sensor onto the stapedius muscle or tendon. The sensing device should be small and adapted to the size of the muscle or tendon. But, after a stimulating electrode has been inserted into the cochlea, it is difficult to bring a sensing device to the tendon with typical surgical tools. The space is very tight and any movement to approach the tendon or muscle carries a risk of displacing the inserted cochlear stimulating electrode.

Embodiments of the present invention provide an implantable fixation structure to fix and attach one or more cochlear implant elements such as electronic sensors, additional implantable electrodes, electro-mechanical actuators (e.g. Floating Mass Transducer), implantable microphones or other arbitrary devices, and bring them into contact with the stapedius muscle/tendon or other structures in the middle ear, after an electrode array has been inserted into the cochlea. Thus, an implantable fixation structure includes at least one implantable holding element, which is connected to an implantable cochlear implant element and maintains the cochlear implant element in a desired position relative to the middle ear of a patient user.

Figure 1:
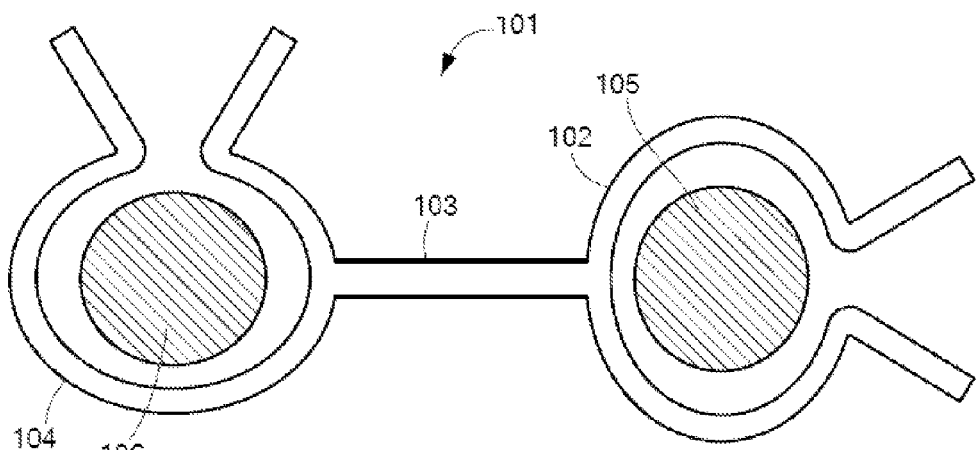
FIG. 1 shows an implantable fixation structure including a fixation clip which is attached to the bony bridge.

FIG. 1 shows an embodiment of an implantable fixation structure 101 with only a single holding element. In this case, an anchoring element in the form of a u-shaped fixation clip 102 is attached to the bony bridge 105 of the middle ear to maintain the fixation structure 101 in a desired position relative to the structures of the middle ear. The fixation clip 102 is connected through a positioning bar 103 with a holding element, u-shaped coupling clip 104 that is perpendicular to the fixation clip 102. After the fixation structure 101 is attached to the bony bridge 105, a cochlear implant element 106 such as an electronic sensor or electro-mechanical actuator can be attached to the coupling clip 104. The thin positioning bar 103 acts as a position adjuster which allows for horizontal and vertical movements within a given range until a desired optimal position is found for the cochlear implant element 106. In other specific embodiments, the anchoring element may use crimping, clipping, gluing, sticking, and/or screwing to maintain the fixation structure 101 in the desired implanted position.

Figure 2:
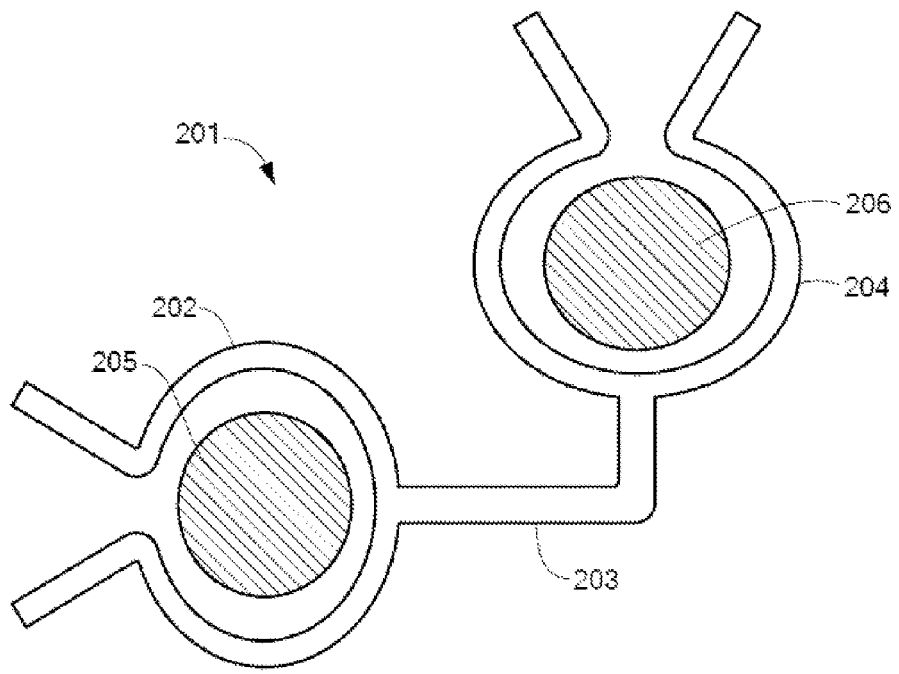
FIG. 2 shows an implantable fixation structure similar to FIG. 1 with a fixation clip that is attached to a cochlear electrode array.

FIG. 2 shows another embodiment of an implantable fixation structure 201 similar to that of FIG. 1 with a fixation clip 202 that is attached to a stimulation electrode array 205. A thin positioning bar 203 connects the fixation clip 202 to a coupling clip 204 for mounting of a cochlear implant element 206 that is perpendicular to the fixation clip 202. After the fixation structure 201 is attached to the stimulation electrode array 205, the cochlear implant element 206 is connected to the coupling clip 204.

Figure 3A:
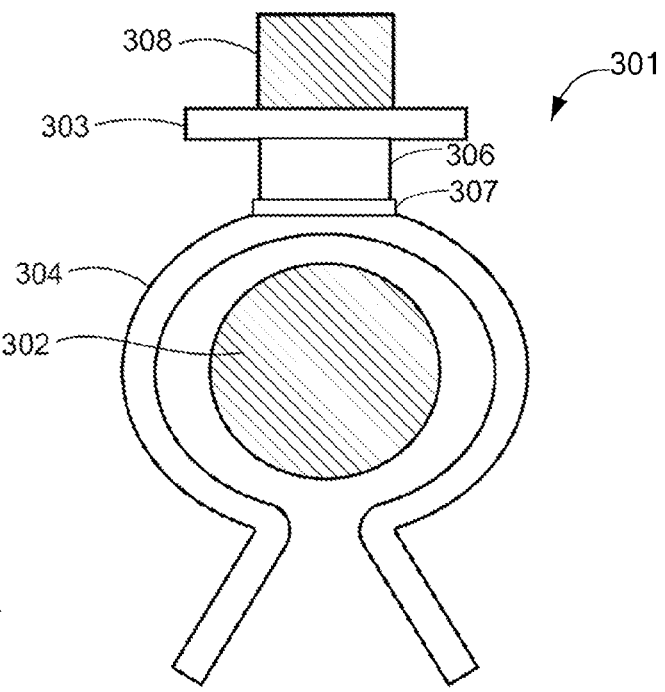
FIG. 3a shows a front view of an implantable fixation structure with a platform for mounting other devices, and which is attached to a cochlear electrode array.
Figure 3B:
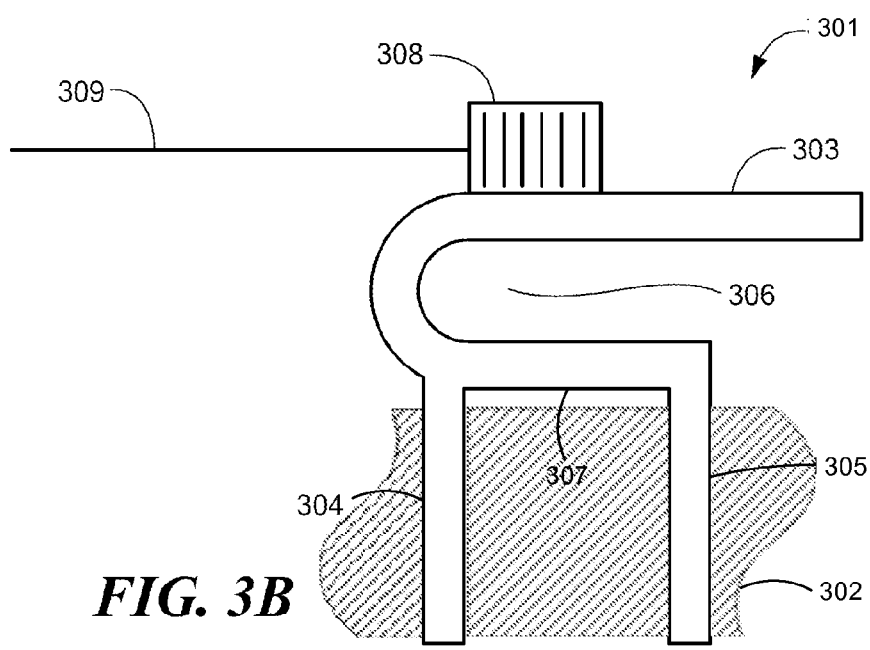
FIG. 3b shows the fixation structure of FIG. 3a in a side view.

FIGS. 3A and 3B show an embodiment of a fixation structure 301 for carrying two cochlear implant elements. Two fixation clips 304 and 305 are attached to a stimulation electrode array 302. Coupling platform 303 is connected to the two fixation clips 304 and 305 by a thin positioning bar 306 which allows for horizontal and vertical position adjustments in a given range. The fixation clips 304 and 305 are connected through a thin connecting bar 307. A first sensor device 308 is connected to the top of the coupling platform 303. A sensor cantilever 309 engages the stapedius tendon.

Figure 4A:
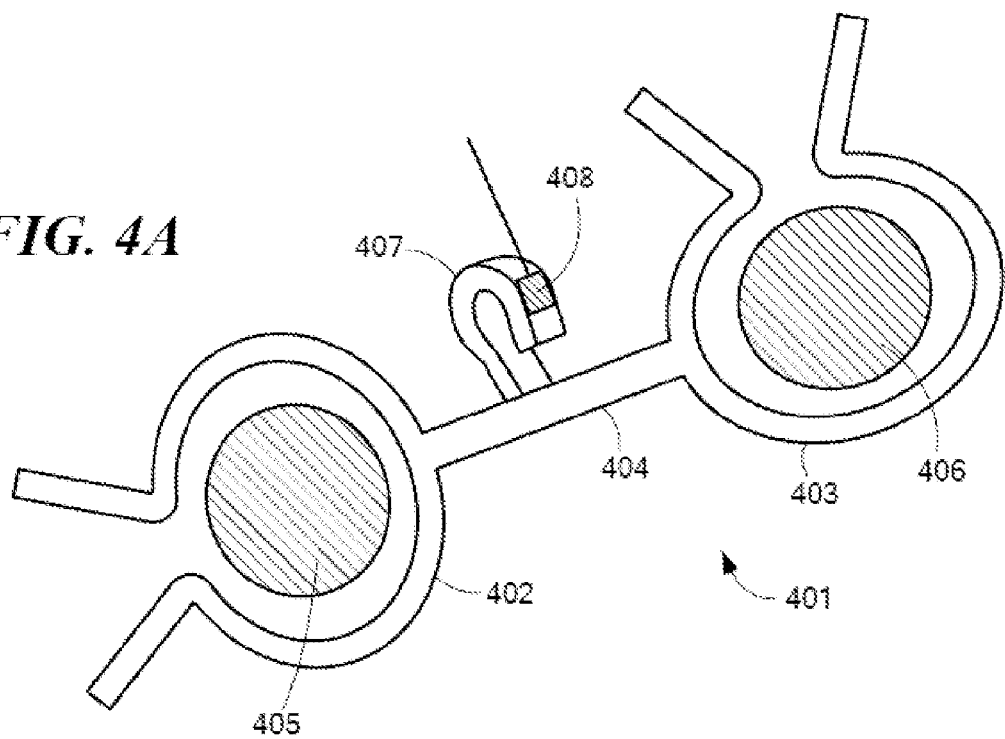
FIG. 4A shows an embodiment of an implantable fixation structure including two fixation clips attached to the bony bridge and the stimulation electrode array, and provided with a platform which is situated in the middle of the bar structure.

FIG. 4A shows the embodiment of another fixation structure 401 including two fixation clips 402 and 403 which are orientated perpendicular to each other. The first fixation clip 402 is attached to a stimulation electrode array 405 and the other fixation clip 403 is attached to the bony bridge 406. Both fixation clips 402 and 403 are connected together through a positioning bar 404. A part of the bar structure is rolled up as shown in FIG. 4A to afford a coupling platform 407 on which a sensor device 408 is placed. The connection of the coupling platform 407 compared to the positioning bar 404 is thin enough to provide for horizontal and vertical position adjustments in a given range and stiff enough to ensure stabilization.

Figure 4B:
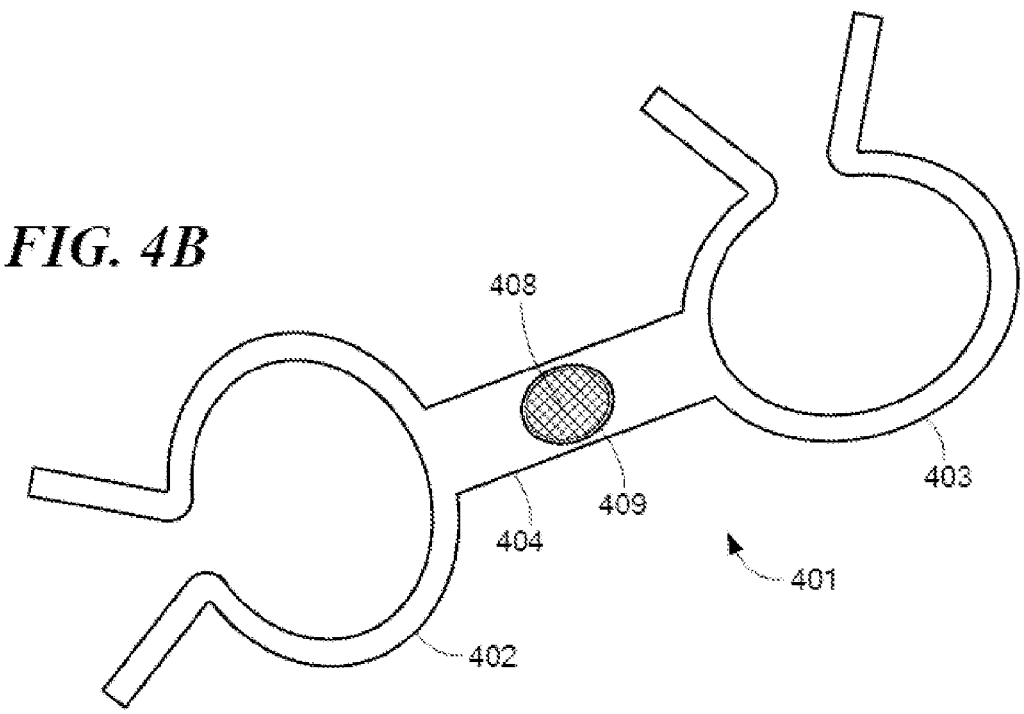
FIG. 4B shows an implantable fixation structure similar to the one in FIG. 4a, with a hole in the middle of the bar structure.

FIG. 4B shows a fixation structure similar to FIG. 4A which includes a coupling hole 409 in the positioning bar 404 instead of a coupling platform 407. The coupling hole 409 surrounds and attaches at least a portion of the cochlear implant element, sensor 408. Due to the coupling hole 409, the positioning bar 404 may benefit from reinforcement with additional material. Once the cochlear implant element has been placed in an optimal position, the positioning bar 404 is crimped with a small gripper to attach the sensor 408 to the fixation structure.

Figure 4C:
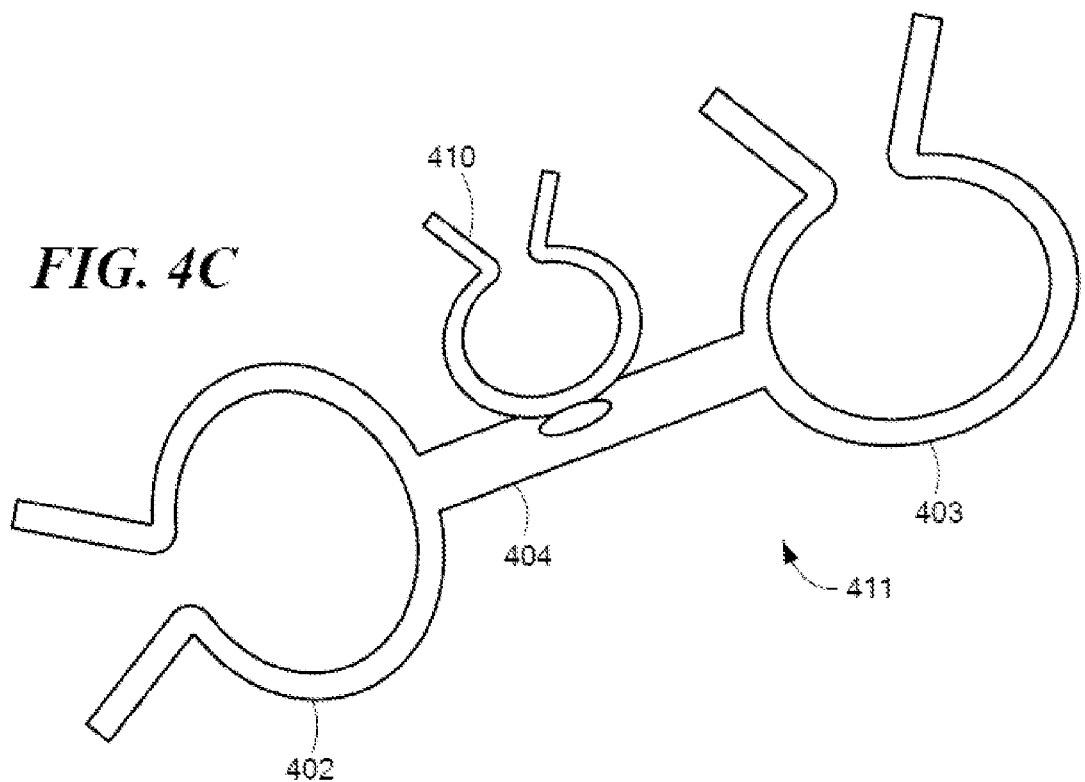
FIG. 4C shows an implantable fixation structure similar to the one in FIG. 4a, with a clip in the middle of the bar structure.

FIG. 4C shows a fixation structure 411 which is similar to 401 (FIG. 4A) including two fixation clips 402 and 403 with a connecting bar 404 in between. A coupling clip 410 is situated perpendicular to the bar structure 404. After the fixation structure 411 is attached to the bony bridge 406 and the stimulation electrode array 405, a cochlear implant element is plugged into the coupling clip 410.

Figure 4D:
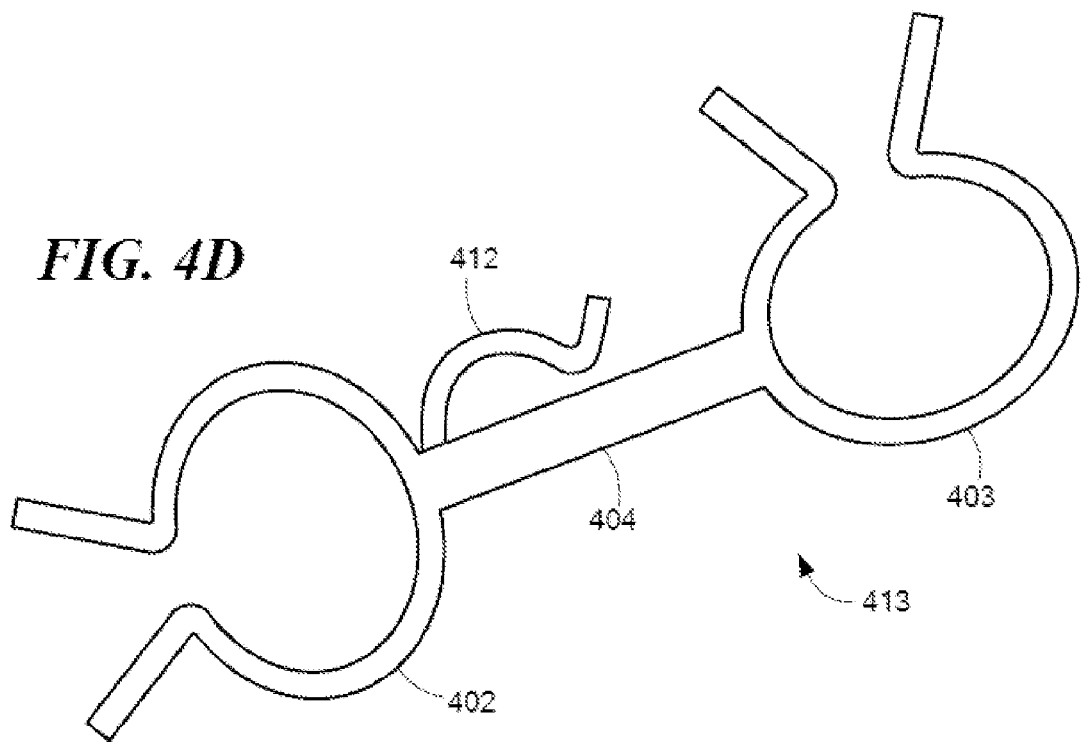
FIG. 4D shows an implantable fixation structure similar to the one in FIG. 4a, with a pen-ball clip in the middle of the bar structure.

FIG. 4D shows a fixation structure 413 which is similar to 401 including two fixation clips 402 and 403 and a connecting bar 404 in between. A rolling clip 412 is situated perpendicular to the bar structure 404 for fixing a cochlear implant element. The rolling clip 412 has a wave-like shape which is open on one side to insert the corresponding device. After the fixation structure 413 is attached to the stimulation electrode array 405 and bony bridge 406 or other middle ear structure, the cochlear implant element is plugged laterally into the rolling clip 412.

Figure 5A:
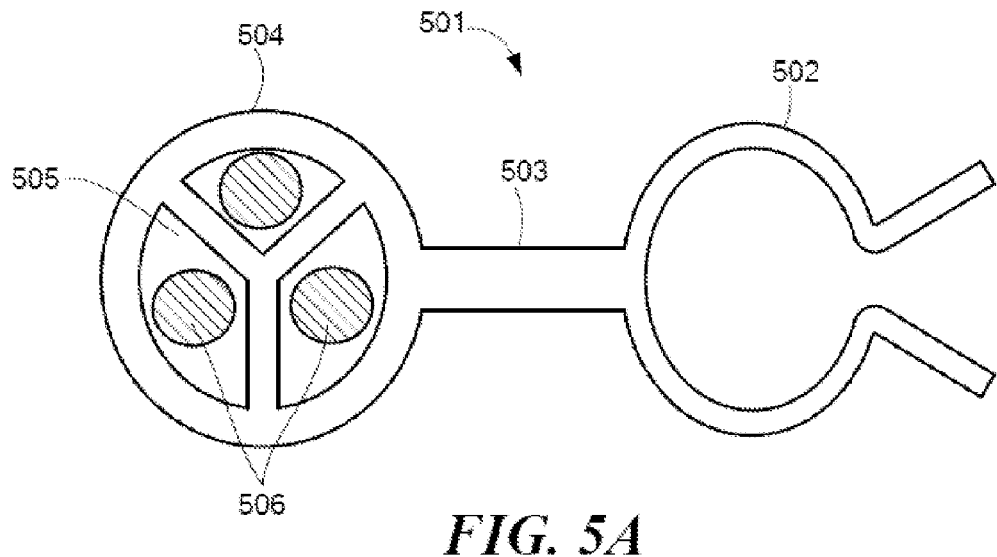
FIG. 5A shows an implantable fixation structure including a clip and a ring-shaped structure.

FIG. 5A shows a fixation structure 501 which has a similar fixation clip 502 like the one shown in FIG. 1. A positioning bar 503 connects the fixation clip 502 with a ring-shaped holder 504 which looks like a spoke wheel. In one embodiment, the fixation clip 502 is orientated perpendicular to the ring-shaped holder 504. The ring-shaped holder 504 is divided into several ring segments 505—for example, two, three or four ring segments—which allow for coupling of one or more sensors, actuators and/or stimulation electrode array 506.

Figure 5B:
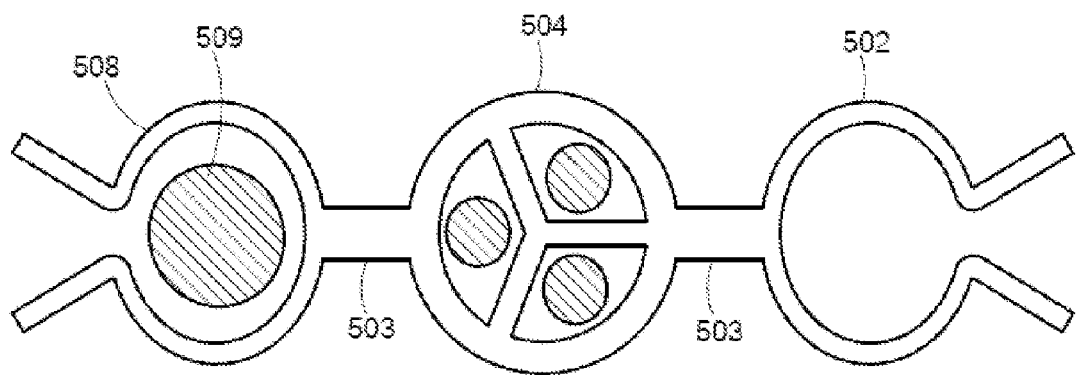
FIG. 5B shows an implantable fixation structure including two clips and a ring-shaped holder situated in the middle.

FIG. 5B shows an embodiment of a fixation structure 507 similar to FIG. 5A comprising of a further fixation clip 508 which is attached to the stimulation electrode array 509. The fixation clips 502 and 508 are connected to the ring-shaped holder 504 through a small bar structure 503.

Figure 6:
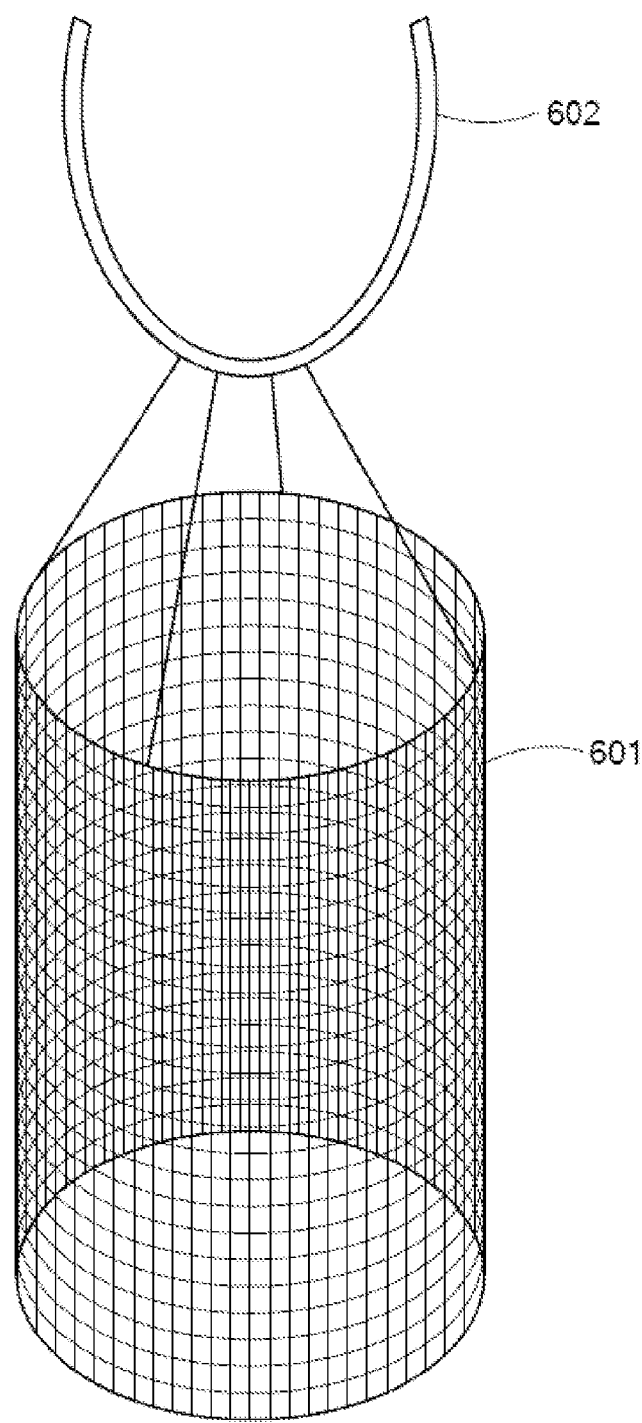
FIG. 6 shows an implantable fixation structure including a wire gauze stent-like tube and a clip on one side.

FIG. 6 shows a stent-like tube 601 composed of wire gauze. The stent-like tube 601 has a larger diameter than the average mastoidectomy. A coupling clip 602 fixes in place a cochlear implant element. The coupling clip 602 is attached to and inside the stent-like tube 601.

Figure 7A:
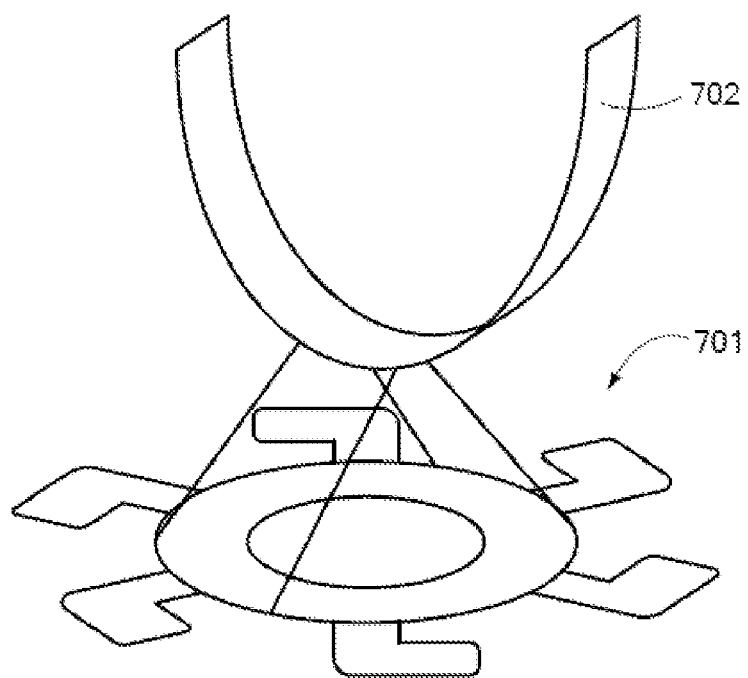
FIGS. 7A and 7B show a tentacle structure embodiment of an implantable fixation structure.
Figure 7B:
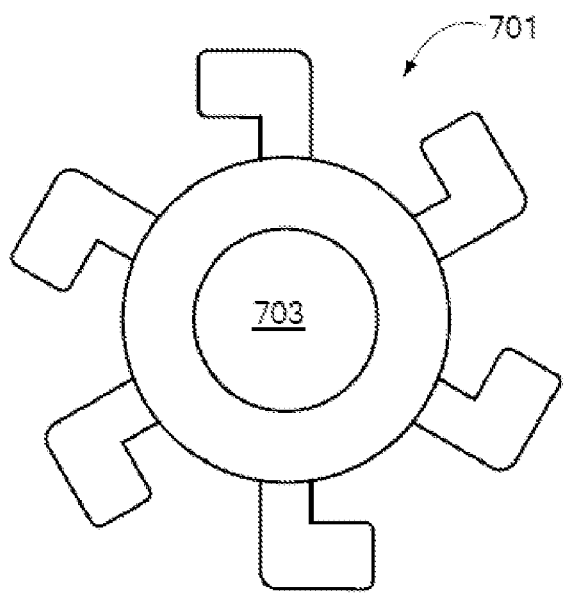

FIGS. 7A and 7B show a flexible tentacle structure 701 which is insertable into a mastoidectomy. FIG. 7A shows the fixation device from a front view, and FIG. 7B shows the same tentacle structure from above. Due to the flexible tentacles, a fixed anchorage is given in the mastoidectomy. A coupling clip 702 or mounting platform 703 is attached to the tentacle structure to attach a cochlear implant element.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable fixation structure comprising:
a c-shape bone fixation clip adapted to fit over and attach to a bony bridge element in a middle ear of a patient;
a c-shape electrode fixation clip adapted to fit over and attach to an electrode array element in the middle ear of the patient;
a connecting bar having a first end connected to the bone fixation clip and a second end connected to the electrode fixation clip; and
a coupling clip connected to the connecting bar between the first end and the second end and adapted to fit over and attach to a cochlear implant element and hold the cochlear implant element in a desired position relative to the middle ear of the patient.

2. An implantable fixation structure according to claim 1, wherein the cochlear implant element includes at least one of an electronic sensor and an electro-mechanical actuator.

3. An implantable fixation structure according to claim 1, wherein the cochlear implant element includes at least one of an implantable electrode and an implantable microphone.

4. An implantable fixation structure according to claim 1, wherein the cochlear implant element includes a stapedius reflex sensor.

5. An implantable fixation structure according to claim 1, wherein the coupling clip is connected perpendicular to the connecting bar.

6. A cochlear implant system having an implantable fixation structure according to any of claims 1-5.

* * * * *